United States Patent
Bode et al.

(10) Patent No.: US 11,896,603 B2
(45) Date of Patent: Feb. 13, 2024

(54) OLIGOSACCHARIDE AS THERAPEUTIC AGENT FOR ALCOHOL ASSOCIATED LIVER DISEASE

(71) Applicant: The Regents of the University of California, Oakland, CA (US)

(72) Inventors: Lars Bode, San Diego, CA (US); Bernd Schnabl, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 147 days.

(21) Appl. No.: 17/346,070

(22) Filed: Jun. 11, 2021

(65) Prior Publication Data
US 2021/0386765 A1 Dec. 16, 2021

Related U.S. Application Data

(60) Provisional application No. 63/038,258, filed on Jun. 12, 2020.

(51) Int. Cl.
| | | |
|---|---|---|
| *A61K 31/702* | (2006.01) | |
| *A61K 9/00* | (2006.01) | |
| *A61K 45/06* | (2006.01) | |
| *A61P 31/04* | (2006.01) | |
| *A61K 31/522* | (2006.01) | |
| *A61K 31/145* | (2006.01) | |
| *A61P 1/16* | (2006.01) | |

(52) U.S. Cl.
CPC .......... *A61K 31/702* (2013.01); *A61K 9/0053* (2013.01); *A61K 31/145* (2013.01); *A61K 31/522* (2013.01); *A61K 45/06* (2013.01); *A61P 1/16* (2018.01); *A61P 31/04* (2018.01)

(58) Field of Classification Search
CPC .. A61K 31/702; A61K 31/145; A61K 31/522; A61K 9/0053; A61K 45/06; A61P 1/16; A61P 31/04
USPC .......................................................... 514/61
See application file for complete search history.

(56) References Cited

FOREIGN PATENT DOCUMENTS

| WO | WO 2019/090182 | * | 5/2019 |
| WO | WO-2019106620 A1 | * | 6/2019 |

OTHER PUBLICATIONS

Cave et al. (Environ Health Perspect 118:1735-1742 (2010); Online Sep. 3, 2010).*
Du et al. (World J Gastroenterol Jan. 14, 2014; 20(2): 569-577).*
Duan et al. (Nature | vol. 575 | Nov. 21, 2019 | 505-511).*
Pickard et al. (J Immunol. Jun. 15, 2015; 194(12): 5588-5593).*
Park et al. Pentoxifylline vs. corticosteroid to treat severe alcoholic hepatitis: A randomised, non-inferiority, open trial. Journal of Hepatology 2014 vol. 61, pp. 792-798. (Year: 2014).*

* cited by examiner

*Primary Examiner* — Yih-Horng Shiao
(74) *Attorney, Agent, or Firm* — Gavrilovich, Dodd & Lindsey LLP

(57) ABSTRACT

The disclosure provides for the use of an oligosaccharide for the treatment of liver disease. More particularly, the disclosure provide methods and composition for treating liver disease comprising administering 2'-FL to a subject.

19 Claims, 9 Drawing Sheets

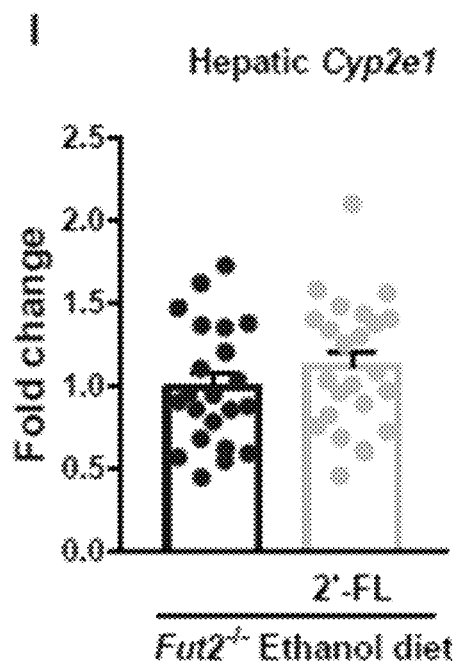
FIG. 4I
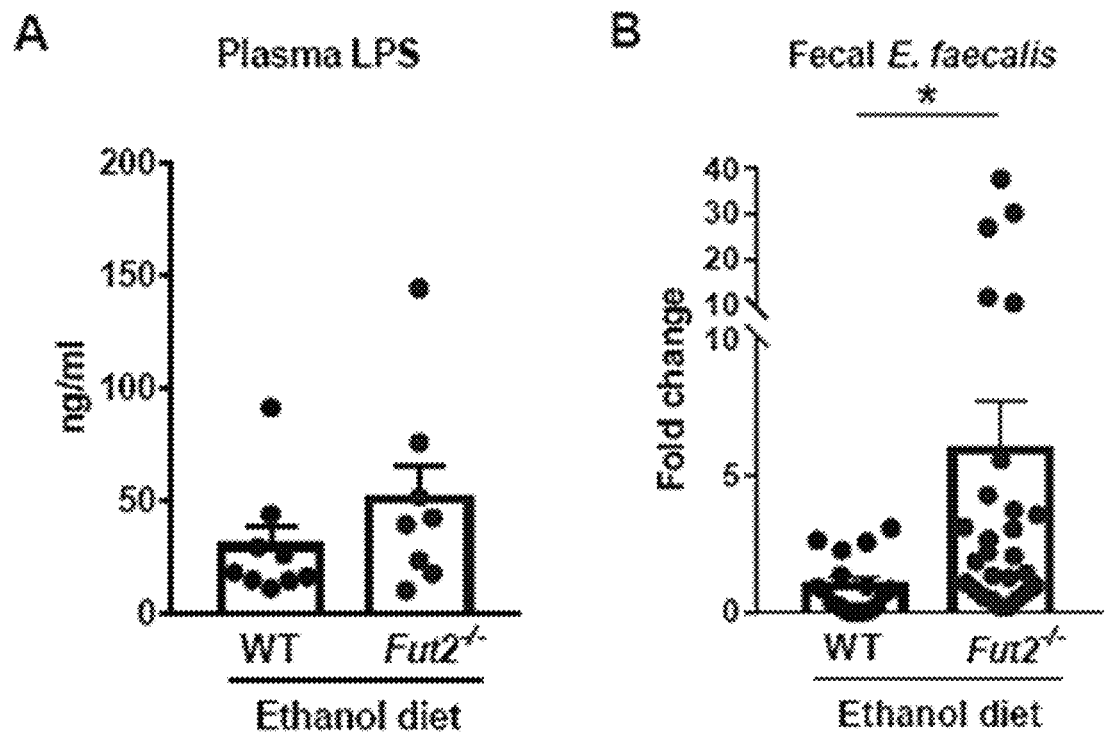
FIG. 5A
FIG. 5B

OLIGOSACCHARIDE AS THERAPEUTIC AGENT FOR ALCOHOL ASSOCIATED LIVER DISEASE

CROSS REFERENCE TO RELATED APPLICATIONS

This application claims priority under 35 U.S.C. § 119 from Provisional Application Ser. No. 63/038,258, filed Jun. 12, 2020, the disclosures of which are incorporated herein by reference.

TECHNICAL FIELD

The disclosure provides methods of diagnosing risk of or a cause of alcohol induced liver disease as well as method for the use of an oligosaccharide for the treatment of liver disease.

BACKGROUND

Human mother's milk contains lactose as well as a complex mixture of oligosaccharides called Human Milk Oligosaccharides (HMO). This oligosaccharide fraction of human mother's milk is unique with respect to composition and quantity. In contrast to other mammals, human mother's milk comprises an oligosaccharide concentration ranging from 7 to 12 g/L, which is by a factor of 10 to 100 higher than in most other mammals (Boehm & Stahl, 2007, Kunz et al., 2000, Newburg & Neubauer, 1995). Today, more than 80 compounds, belonging to HMOs, have been structurally characterized. Generally, HMOs are characterized, unlike other oligosaccharides found in the human body, by a lactose moiety at the reducing end, and fucose and/or sialic acid at the non-reducing end. Two basic types are distinguished: Oligosaccharides of type I structure have fucose α-1,4-linked to GlcNAc, whereas those of type II structure show α-1,3-fucosylation of GlcNAc or glucose; either type may contain α-1,2-linked fucose to galactose. The most prominent oligosaccharides are 2'-fucosyllactose and 3-fucosyllactose.

SUMMARY

The disclosure establishes that intestinal α1-2-fucosylation acts as a host protective mechanism against ethanol-induced liver disease. 2'-FL, an oligosaccharide naturally present in human milk, is a prebiotic that could be considered as therapeutic agent for alcohol-associated liver disease. In particular, the studies presented herein show that intestinal α1-2-fucosylation was down-regulated in patients with alcohol use disorder. Further, in the studies presented herein show that the lack of α1-2-fucosylation in Fut2 deficient mice exacerbates ethanol-induced liver injury, steatosis and inflammation without affecting ethanol metabolism. Moreover, additional studies presented herein demonstrate that dietary supplementation of the al-2-fucosylated glycan 2'-fucosyllactose ameliorates ethanol-induced liver disease in Fut2 deficient mice. Finally, studies show that despite no direct effects on growth of *Enterococcus faecalis* in vitro, intestinal α1-2-fucosylation reduces colonization of cytolysin-positive *E. faecalis* in the intestine of ethanol-fed mice.

In a particular embodiment, the disclosure provides a method for treating a subject with liver disease, comprising administering to the subject an effective amount of an oligosaccharide, or a pharmaceutical composition comprising the oligosaccharide, wherein the oligosaccharide comprises a structure of Formula I:

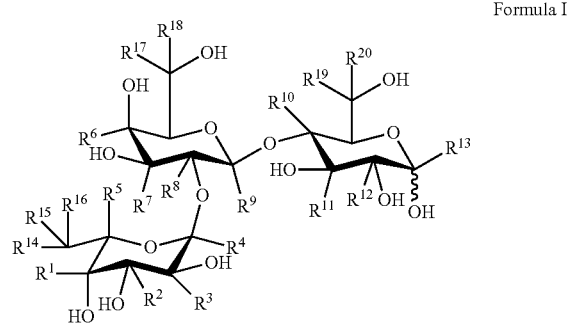

Formula I or a pharmaceutically acceptable salt, polymorph, solvate, or prodrug thereof, wherein:

$R^1$-$R^{20}$ are independently selected from H, D, halo, azide, nitro, amine, aldehyde, alkoxy, ketone, ester, carboxylic acid, hydroxyl, optionally substituted ($C_1$-$C_6$)alkyl, optionally substituted ($C_1$-$C_6$)heteroalkyl, optionally substituted ($C_2$-$C_6$)alkenyl, optionally substituted ($C_2$-$C_6$)heteroalkenyl, optionally substituted ($C_2$-$C_6$)alkynyl, optionally substituted ($C_2$-$C_6$)heteroalkynyl, and heterocycle. In a further embodiment, the oligosaccharide comprises a structure of Formula I(a):

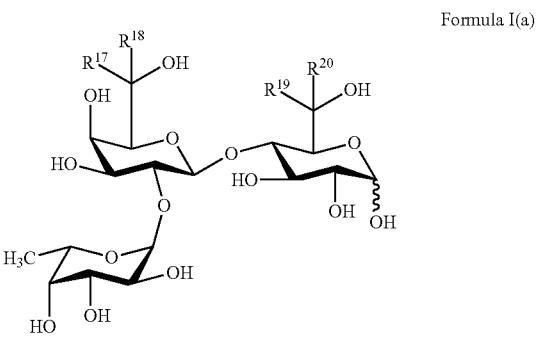

Formula I(a)

or a pharmaceutically acceptable salt, polymorph, solvate, or prodrug thereof, wherein: $R^{17}$-$R^{20}$ are independently selected from H, D, halo, azide, nitro, amine, aldehyde, alkoxy, ketone, ester, carboxylic acid, hydroxyl, optionally substituted ($C_1$-$C_6$) alkyl, optionally substituted ($C_1$-$C_6$) heteroalkyl, optionally substituted ($C_2$-$C_6$)alkenyl, optionally substituted ($C_2$-$C_6$)heteroalkenyl, optionally substituted ($C_2$-$C_6$)alkynyl, optionally substituted ($C_2$-$C_6$)heteroalkynyl, and heterocycle. In yet a further embodiment, the oligosaccharide comprises a structure of Formula I (b):

Formula I(b)

[Chemical structure of Formula I(b)]

or a pharmaceutically acceptable salt, polymorph, solvate, or prodrug thereof. In another embodiment, the oligosaccharide or the pharmaceutical composition comprising the oligosaccharide is orally administered to the subject. In yet another embodiment, the oligosaccharide is orally administered to the subject as part of a nutritional composition. In a certain embodiment, the pharmaceutical composition comprising the oligosaccharide is formulated as a tablet or a capsule. In a further embodiment, the nutritional composition comprises at least 9% of the oligosaccharide in the nutritional composition. In yet a further embodiment, the liver disease is caused by chronic and/or excessive alcohol consumption or by ingestion of harmful chemicals. Examples of harmful chemicals include, but are not limited to, vinyl chloride, heavy metals, polychlorinated biphenyls (PCBs), and pesticides. In another embodiment, the oligosaccharide or the pharmaceutical composition comprising the oligosaccharide is administered sequentially or concurrently with one or more liver disease treatments. Examples of liver disease treatments include, but are not limited to, corticosteroids, cyteamine and/or cystamine, and pentoxifylline.

In a certain embodiment, the disclosure also provides a method to restore or compensate for the loss α1-2-fucosylated glycans on the surface of a subject's intestinal epithelial cells caused by excessive and/or chronic alcohol consumption or by ingestion of harmful chemicals, comprising: administering to the subject an effective amount of an oligosaccharide, or a pharmaceutical composition comprising the oligosaccharide, wherein the oligosaccharide comprises a structure of Formula I:

Formula I

[Chemical structure of Formula I with R¹-R²⁰ substituents]

or a pharmaceutically acceptable salt, polymorph, solvate, or prodrug thereof, wherein: $R^1$-$R^{20}$ are independently selected from H, D, halo, azide, nitro, amine, aldehyde, alkoxy, ketone, ester, carboxylic acid, hydroxyl, optionally substituted ($C_1$-$C_6$) alkyl, optionally substituted ($C_1$-$C_6$)heteroalkyl, optionally substituted ($C_2$-$C_6$)alkenyl, optionally substituted ($C_2$-$C_6$)heteroalkenyl, optionally substituted ($C_2$-$C_6$)alkynyl, optionally substituted ($C_2$-$C_6$)heteroalkynyl, and heterocycle. In another embodiment, the oligosaccharide comprises a structure of Formula I (b):

Formula I(b)

[Chemical structure of Formula I(b)]

or a pharmaceutically acceptable salt, polymorph, solvate, or prodrug thereof. In yet another embodiment, the oligosaccharide or the pharmaceutical composition comprising the oligosaccharide is orally administered to the subject. In a further embodiment, the oligosaccharide is orally administered to the subject as part of a nutritional composition. In yet a further embodiment, the pharmaceutical composition comprising the oligosaccharide is formulated as a tablet or a capsule. In a certain embodiment, the nutritional composition comprises at least 9% of the oligosaccharide in the nutritional composition.

In yet some other alternative embodiments of any of the foregoing, the administering results in improvement in liver function compared to levels before administration of the oligosaccharide composition. In another embodiment, the administering results in a reduction in the incidence of or progression of cirrhosis. In yet another embodiment, the administering results in a reduction in the incidence of hepatocellular carcinoma. In still yet another embodiment, the administering results in a decrease in hepatic aminotransferase levels compared to levels before administration of the oligosaccharide composition. In still another embodiment, the administering results in a reduction in hepatic transaminase of between approximately 10% to 40% compared to levels before treatment. In yet other embodiments of the foregoing the administering results in a reduction in alanine aminotransferase levels in a treated patient to approximately 30%, 20% or 10% above normal ALT levels, or at normal ALT levels (≥40 iu/L). In yet another embodiment, the administering results in a reduction in aspartate aminotransferase levels in a treated patient to approximately 30%, 20% or 10% above normal AST levels or to normal AST levels. In another embodiments, the administering results in a reduction in serum ferritin levels compared to levels before treatment with the oligosaccharide composition.

The disclosure also provides a method comprising obtaining a sample from the gastrointestinal tract of a subject having aberrant liver function, determining the level of 2'FL, E. faecalis and/or cytolysin in the sample, if the sample shows one or more of low 2FL, high E. Faecalis or high cytolysin, administering a composition comprising 2'FL to the subject.

DESCRIPTION OF DRAWINGS

FIG. 4A-I. 2'-FL supplementation attenuates ethanol-induced liver disease in the intestine of Fut2 deficient mice. $Fut2^{-/-}$ mice were assigned to 2'-fucosyllactose (2'-FL) treated group and control group, and fed with chronic-binge ethanol diet. In the 2'-FL treated group, 2'-FL (2 mg/mL) was supplemented continuously in the ethanol diet. The experimental diet and 2'-FL treatment lasted for 2 weeks. (A) Plasma alanine aminotransferase (ALT). (B) Hepatic triglycerides levels. (C) Representative images of H&E-stained liver tissue. (D) Hepatic Cxcl1 mRNA. (E) Hepatic Cxcl2 mRNA. (F) Representative images of Oil Red O-stained liver tissue. (G) Plasma ethanol. (H) Hepatic expression of Adh1 mRNA. (I) Hepatic expression of Cyp2e1 mRNA. Data represent mean±SEM; * and ** indicate P<0.05 and P<0.01, respectively. Scale bar=50 μm. Experiments performed in n=18-24 per group. For the H&E and Oil Red O staining, n=10 per group.

FIG. 5A-G demonstrates the effects of Fut2 deficiency and 2'-FL supplementation on systemic endotoxin and intestinal *E. faecalis* and cytolysin. (A)-(C) $Fut2^{-/-}$ and wild type (WT) littermates were fed with ethanol-containing Lieber DeCarli diet for 9 weeks. (D)-(F) $Fut2^{-/-}$ mice were fed with chronic-binge ethanol diet with or without 2'-FL for 2 weeks. (A) and (D) Plasma LPS. (B) and (E) Fecal *E. faecalis*. (C) and (F) Fecal cytolysin. (G) A cytolysin-positive *E. faecalis* strain was incubated with different concentrations of 2'-FL for 6 hours, and OD600 was measured every 30 minutes. Growth curve of *E. faecalis*. Data represent mean±SEM, * indicate P<0.05. (A)-(F) Experiments performed in n=8-28 per group. (G) Experiments performed in triplicate and repeated for 3 times. A representative growth curve is shown.

DETAILED DESCRIPTION

Figure 1:
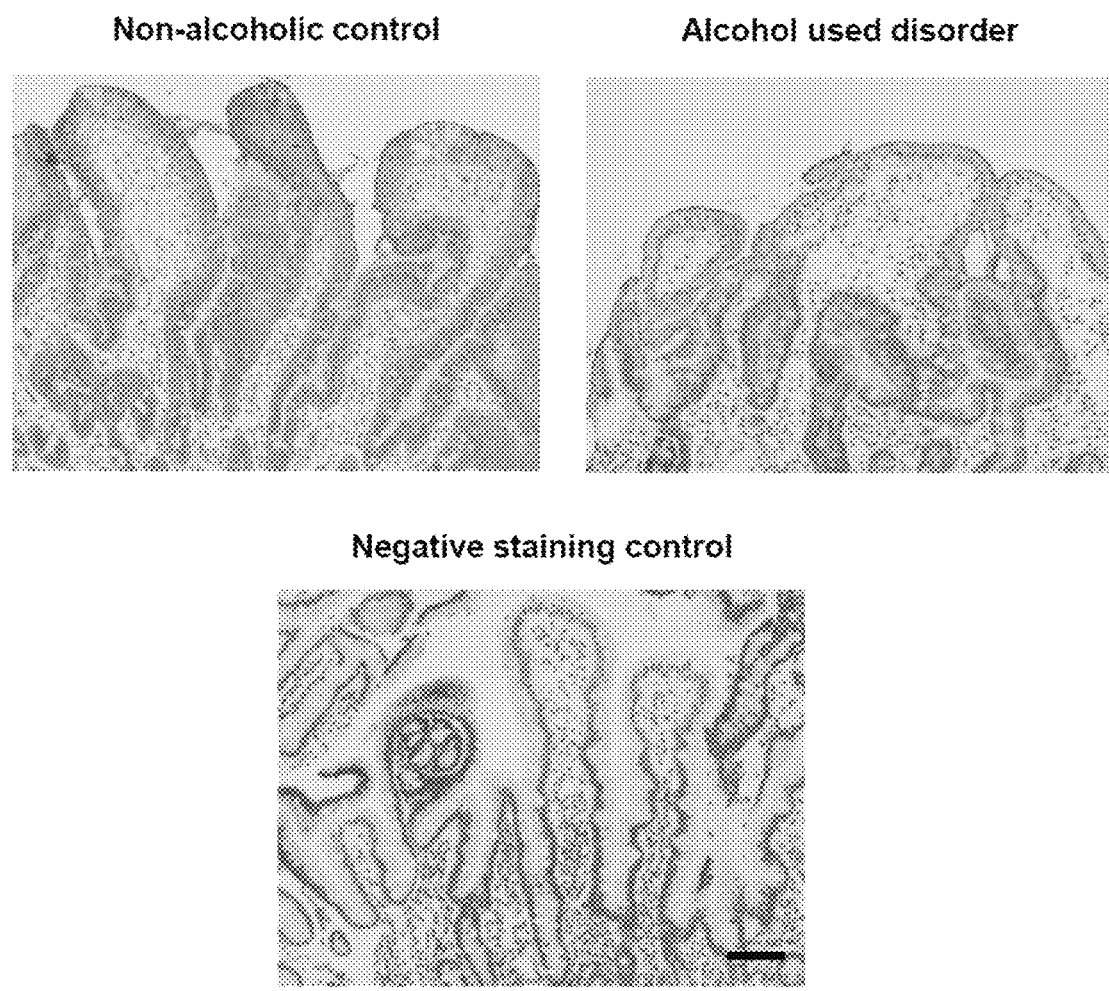
FIG. 1 demonstrates decreased intestinal α1-2-fucosylation in patients with alcohol use disorder. The expression of intestinal α1-2-fucosylation was determined on duodenal biopsies obtained from patients with alcohol use disorder (n=10) and non-alcoholic controls (n=11) using *Ulex Europaeus* Agglutinin I (UEA) staining. A negative staining control was performed by using PBS instead of UEA. Representative intestinal sections are shown. Scale bar=50 μm.

As used herein and in the appended claims, the singular forms "a," "an," and "the" include plural referents unless the context clearly dictates otherwise. Thus, for example, reference to "an oligosaccharide" includes a plurality of such oligosaccharides and reference to "the therapeutic agent" includes reference to one or more therapeutic agents and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, for terms expressly defined in this disclosure, the definition of the term as expressly provided in this disclosure will control in all respects, even if the term has been given a different meaning in a publication, dictionary, treatise, and the like.

The terms "active ingredient" and "active substance" refer to an oligosaccharide or compound, which is administered, alone or in combination with one or more pharmaceutically acceptable excipients and/or carriers, to a subject for treating, preventing, or ameliorating one or more symptoms of a disorder.

The term "cytolysin" refers to a two-subunit bacteriocin secreted by *Enterococcus faecalis*.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O. In a particular embodiment, a "hetero"-hydrocarbon (e.g., alkyl, alkenyl, alkynyl) refers to a hydrocarbon that has from 1 to 3 C, N and/or S atoms as part of the parent chain.

The term "heterocycle," as used herein, refers to ring structures that contain at least 1 noncarbon ring atom. A "heterocycle" for the purposes of this disclosure encompass from 1 to 4 heterocycle rings, wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In the case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

"Human milk oligosaccharide" or "HMO" means a complex carbohydrate found in human breast milk. HMOs typically have a core structure comprising a lactose unit at the reducing end that can be elongated by one or more β-N-acetyl-lactosaminyl and/or one or more lacto-N-biosyl units, and which core structure can be substituted by an αL-fucopyranosyl and/or an α-N-acetyl-neuraminyl (sialyl) moiety. In this regard, non-acidic (or neutral) HMOs are devoid of a sialyl residue, and the acidic HMOs have at least one sialyl residue in their structure. Examples of neutral fucosylated HMOs include 2'-fucosyllactose (2'-FL), lacto-N-fucopentaose I (LNFP-I), lacto-N-difucohexaose I (LNDFH-I), 3'-fucosyllactose (3'-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI) lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), and 3-fucosyl-3'-sialyllactose (FSL). The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. 2'-FL can be made as described in WO 2010/115934 and WO 2010/115935. Fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified E. coli.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "non-release controlling excipient" as used herein, refers to an excipient whose primary function do not include modifying the duration or place of release of the active substance from a dosage form as compared with a conventional immediate release dosage form.

The term "optionally substituted" refers to a functional group, typically a hydrocarbon or heterocycle, where one or more hydrogen atoms may be replaced with a substituent. Accordingly, "optionally substituted" refers to a functional group that is substituted, in that one or more hydrogen atoms are replaced with a substituent, or unsubstituted, in that the hydrogen atoms are not replaced with a substituent. For example, an optionally substituted hydrocarbon group refers to an unsubstituted hydrocarbon group or a substituted hydrocarbon group.

The term "pharmaceutically acceptable carrier," "pharmaceutically acceptable excipient," "physiologically acceptable carrier," or "physiologically acceptable excipient" as used herein, refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. Examples of "pharmaceutically acceptable carriers" and "pharmaceutically acceptable excipients" can be found in the following, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004.

The term "release controlling excipient" as used herein, refers to an excipient whose primary function is to modify the duration or place of release of the active substance from a dosage form as compared with a conventional immediate release dosage form.

The term "subject" as used herein, refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein. For example, a mammalian subject can refer to a human patient.

The term "substituent" refers to an atom or group of atoms substituted in place of a hydrogen atom. For purposes of this invention, a substituent would include deuterium atoms.

The term "substituted" with respect to hydrocarbons, heterocycles, and the like, refers to structures wherein the parent chain contains one or more substituents.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenicity, are commensurate with a reasonable benefit/risk ratio, and are effective for their intended use.

The terms "treat", "treating" and "treatment", as used herein, refers to ameliorating symptoms associated with liver disease, including preventing or delaying the onset of liver disease, and/or lessening the severity or frequency of symptoms of liver disease.

The term "unsubstituted" with respect to hydrocarbons, heterocycles, and the like, refers to structures wherein the parent chain contains no substituents.

Consumption of alcohol has caused 3 million deaths (5.3% of all deaths) worldwide in 2016 according to the WHO, which is higher than that caused by HIV/AIDS and diabetes. Alcohol is one of the most frequent causes of liver disease. Alcohol-associated liver disease includes alcohol-associated steatosis, steatohepatitis, fibrosis and cirrhosis, and alcoholic hepatitis. Acute alcoholic hepatitis with a 90-day mortality of up to 50% and advanced liver cirrhosis with the median survival time of as low as 1-2 years are the most severe subtypes of alcohol-associated liver disease. The gut-liver axis is important for the progression of alcohol-associated liver disease in both patients and experimental models.

The Fut2 gene encodes a galactoside 2-L-fucosyltransferase (fucosyltransferase 2, Fut2) that catalyzes the process of α1-2-fucosylation by adding fucose to glycolipids and glycoproteins as well as unconjugated glycans like human milk oligosaccharides (HMOs). Fut2 is expressed in epithelial cells of the digestive tract while absent in the liver. Fut2 expression is high in the distal gut, which is colonized by a large number of symbiotic microbes. Absence of α1-2-fucosylation at the cell surface of enterocytes and mucus in so-called "non-secretor" subjects may result in alterations in intestinal bacteria, barrier function and pathogen adhesion. Both "non-secretors" and Fut2 deficient mice showed changes in the commensal microbiota and in microbial metabolite profiles. Fucosylated glycans regulate host-microbe interactions. Membrane and secreted α1-2-linked fucose can be cleaved by bacterial fucosidase and the liberated L-fucose is utilized by certain bacteria. For these reasons, Fut2 polymorphism has been implicated in pathogenesis of several diseases that are closely associated with the intestinal microbiome. Non-secretors are more susceptible to Crohn's disease, chronic pancreatitis, primary sclerosing cholangitis and some specific pathogens like *Candida albicans, Haemophilus* influenza and pathogenic *Escherichia coli*. Although intestinal dysbiosis is an important co-factor for progression of alcohol-associated liver disease, the underlying mechanism remains unclear. The role of Fut2-mediated intestinal α1-2-fucosylation in development of alcohol-associated liver disease is demonstrated by this disclosure.

The disclosure shows that alcohol abuse is associated with decreased intestinal α1-2-fucosylation in patients with chronic alcohol use. Eliminating α1-2-fucosylation by using Fut2 deficient mice exacerbates ethanol-induced liver injury, steatosis and inflammation. A dietary approach to restore α1-2-fucosylation with prebiotic α1-2-fucosylated glycans overcomes the absence of intestinal α1-2-fucosylation in Fut2$^{-/-}$ mice and attenuates ethanol-induced liver disease. All the findings presented herein indicate the important role of Fut2 and intestinal α1-2-fucosylation for the pathogenesis of ethanol-induced liver disease in mice. Intestinal α1-2-fucosylation acts as a host protective mechanism against ethanol-induced liver disease.

The disclosure demonstrates that Fut2 mediated intestinal α1-2-fucosylation protects against intestinal colonization and translocation of the pathobiont *E. faecalis* in a chemical-induced colitis mouse model. Colonization of *E. faecalis* in the intestine induces mild liver disease and exacerbates ethanol-induced liver disease in mice. The disclosure shows an association between *E. faecalis* cytolysin positivity in patients with alcoholic hepatitis and mortality. Cytolysin is a bacterial exotoxin produced by *E. faecalis* and it has lytic activity against eukaryotic cells. Ethanol-fed mice gavaged with cytolytic *E. faecalis* had more severe liver disease compared with mice gavaged with non-cytolytic *E. faecalis*. Treatment with phages against cytolysin-positive *E. faecalis* reduces intestinal cytolysin-positive *E. faecalis* and ameliorates ethanol-induced liver disease in gnotobiotic mice colonized with feces from cytolysin-positive patients with alcoholic hepatitis. Cytolysin produced by intestinal *E. faecalis* is important for the pathogenesis of ethanol-induced liver disease (see, U.S. Pat. Publ. No. 2021/0095327, which is incorporated herein by reference). It was observed herein, that there was an increase of intestinal *E. faecalis* and cytolysin in Fut2$^{-/-}$ mice after ethanol diet feeding. This indicates that loss of intestinal α1-2-fucosylation is associated with an increase of intestinal cytolytic *E. faecalis* after ethanol feeding and this could contribute to an exacerbation of liver disease.

The in vitro culture experiments presented herein did not show a direct effect of 2'-FL on growth of cytolytic *E. faecalis*. Although not wishing to be bound by particular mechanism of operation, it is believe that 2'-FL causes an increase in other beneficial bacteria in the intestine, which in turn prevent the colonization of cytolysin-positive *E. faecalis*.

As mentioned above, 2'-FL is an α1-2-fucosylated glycan that is highly abundant in human milk of Secretor women. 2'-FL synthesized in bioengineered microbes has received FDA GRAS status for use in both infants and adults and is currently used as supplement in infant formula to support growth of the infant. As shown herein, 2'-FL reduces ethanol-induced liver disease in Fut2-1-animal models. Accordingly, 2'FL can be used as a safe and low-cost dietary supplement or medical food for patients suffering from alcohol-associated liver disease.

The disclosure demonstrates that 2'FL can be used to treat subjects suffering from alcohol associated liver disease. The disclosure also demonstrates that alcohol misuse decreases intestinal α1-2-fucosylation. Absence of intestinal α1-2-fucosylation allows intestinal growth of cytolysin-positive *E. faecalis*, which contributes to an exacerbation of ethanol-induced liver disease.

Oral administration of an oligosaccharide of the disclosure provides for systemic circulation of the oligosaccharide in a subject. The efficacy of oligosaccharides of disclosure as therapy for treating liver disease is demonstrated herein. Due to the oligosaccharide of the disclosure having little to no adverse effects in humans, this form of therapy could be used as a preventive, as a first line therapy option for liver disease, or as an adjunct to existing liver disease therapies that would be well tolerated by patients of either sex.

In a particular embodiment, the disclosure provides a method for treating a subject with liver disease, comprising administering to the subject an effective amount of an oligosaccharide, or a pharmaceutical composition comprising the oligosaccharide, wherein the oligosaccharide comprises a structure of Formula I:

Formula I

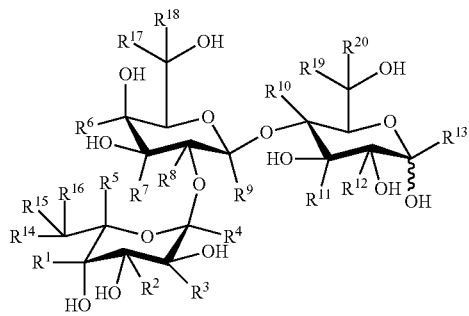

Formula I(b)

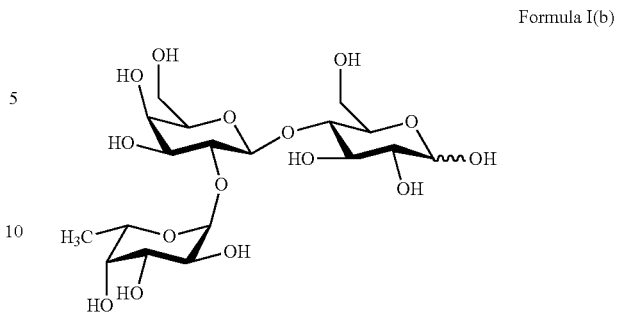

or a pharmaceutically acceptable salt, polymorph, solvate, or prodrug thereof, wherein: $R^1$-$R^{20}$ are independently selected from H, D, halo, azide, nitro, amine, aldehyde, alkoxy, ketone, ester, carboxylic acid, hydroxyl, optionally substituted ($C_1$-$C_6$) alkyl, optionally substituted ($C_1$-$C_6$)heteroalkyl, optionally substituted ($C_2$-$C_6$)alkenyl, optionally substituted ($C_2$-$C_6$)heteroalkenyl, optionally substituted ($C_2$-$C_6$)alkynyl, optionally substituted ($C_2$-$C_6$)heteroalkynyl, and heterocycle.

In another embodiment, the disclosure provides a method for treating a subject with liver disease, comprising administering to the subject an effective amount of an oligosaccharide, or a pharmaceutical composition comprising the oligosaccharide, wherein the oligosaccharide comprises a structure of Formula I(a):

Formula I(a)

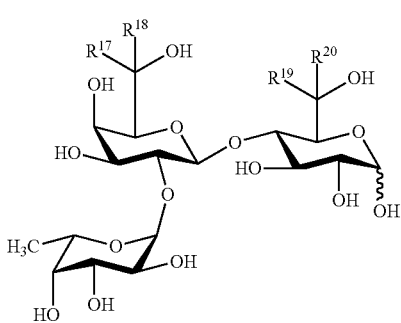

or a pharmaceutically acceptable salt, polymorph, solvate, or prodrug thereof, wherein: $R^{17}$-$R^{20}$ are independently selected from H, D, halo, azide, nitro, amine, aldehyde, alkoxy, ketone, ester, carboxylic acid, hydroxyl, optionally substituted ($C_1$-$C_6$) alkyl, optionally substituted ($C_1$-$C_6$) heteroalkyl, optionally substituted ($C_2$-$C_6$)alkenyl, optionally substituted ($C_2$-$C_6$)heteroalkenyl, optionally substituted ($C_3$-$C_6$)alkynyl, optionally substituted ($C_3$-$C_6$)heteroalkynyl, and heterocycle.

In another embodiment, the disclosure provides a method for treating a subject with liver disease, comprising administering to the subject an effective amount of an oligosaccharide, or a pharmaceutical composition comprising the oligosaccharide, wherein the oligosaccharide comprises a structure of Formula I (b):

or a pharmaceutically acceptable salt, polymorph, solvate, or prodrug thereof.

In a further embodiment, an oligosaccharide disclosed herein is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, substantially an individual diastereomer, or a mixture of about 90% or more by weight of an individual diastereomer and about 10% or less by weight of any other diastereomer.

An oligosaccharide disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of an oligosaccharide in its (R) form is equivalent, for oligosaccharides that undergo epimerization in vivo, to administration of the oligosaccharide in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When an oligosaccharide disclosed herein contains an acidic or basic moiety, it may also be disclosed as a pharmaceutically acceptable salt (See, Berge et al., J. Pharm. Sci. 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

An oligosaccharide disclosed herein may also be designed as a prodrug (e.g., an esterized version of the oligosaccharide), which is a functional derivative of the oligosaccharide as disclosed herein and is readily convertible into the parent oligosaccharide in vivo. Prodrugs are often useful because, in some situations, they may be easier to administer than the parent oligosaccharide. They may, for instance, be bioavailable by oral administration whereas the parent oligosaccharide is not. The prodrug may also have enhanced solubility in pharmaceutical compositions over the parent oligosaccharide. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

An oligosaccharide disclosed herein may be produced by biotechnological means using enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Alternatively, the oligosaccharides may be produced by chemical synthesis from lactose and other substrates.

Biotechnological approaches have made it possible for the large scale, cost-efficient production of target oligosaccharides. Precisely, the oligosaccharides disclosed herein can be produced in high yields in aqueous media by fermentation of genetically modified bacteria, yeasts or other microorganisms. See, for example, WO200104341; WO2007101862, WO2010070104; WO2010142305; WO2012112777; Priem et al., *Glycobiology* 12:235 (2002); Drouillard et al., *Angew. Chem. Int. Ed.* 45:1778 (2006); Han et al., *Biotechnol. Adv.* 30:1268 (2012); Lee et al., *Microb. Cell Fact.* 11:48 (2012); Baumgartner et al., *Microb. Cell Fact.* 12:40 (2013); and WO 2014135167A1. Alternatively, the oligosaccharides of the disclosure can be synthesized based upon methods described in WO2011100980A1; WO2012007588A1; WO2012127410A1; WO2012155916A1; WO2013044928A1; and U.S. Pat. No. 9,102,966B2. 2'-FL can be made as described in WO 2010/115934, WO 2010/115935, and U.S. Pat. No. 9,512,433B2. With regard to biotechnological methods, WO 2001/04341 and WO 2007/101862 describe how to make oligosaccharides optionally substituted by fucose or sialic acid using genetically modified *E. coli*.

In a certain embodiment, the disclosure provides for a nutritional composition that comprises an oligosaccharide disclosed herein along with one or more food grade agents for the treatment of a liver disease in a subject in need thereof. In certain embodiments, the nutritional composition comprises or consists of 2'-FL. In another embodiment, the nutritional composition comprises an oligosaccharide of the disclosure at a percentage of at least 9%, 10%, 15%, 20%, 25%, 30%, 35%, 40%, 45%, 50%, 55%, 60%, 65%, 70%, 75%, 80%, 85%, 90%, 95%, 98%, or a range that includes or is between any two of the foregoing percentages. Examples of food grade agents that can be used with the oligosaccharides disclosed herein, include, but are not limited to, milk (e.g., cow's milk, almond milk, soy milk), yogurt, maltodextrin, milk protein concentrate, Sucromalt, glycerin, cocoa powder, soy protein isolate, fructose, vegetable or animal oils (e.g., high oleic safflower oil, soy oil, canola oil), plant sterol esters, HMSs/HMOs, soy lecithin, carrageenan, taurine, L-carnitine, vitamins and/or minerals (e.g., sodium ascorbate, potassium citrate, sodium phosphate, calcium citrate, choline chloride, potassium chloride, sodium citrate, magnesium oxide, alpha-tocopheryl acetate, zinc sulfate, ferrous sulfate, niacinamide, calcium pantothenate, vitamin A palmitate, citric acid, manganese sulfate, pyridoxine hydrochloride, vitamin D3, copper sulfate, thiamine mononitrate, riboflavin, beta carotene, folic acid, biotin, potassium iodide, chromium chloride, sodium selenate, sodium molybdate, phytonadione, vitamin B12, magnesium chloride, calcium phosphate). In yet another embodiment, the nutritional composition can comprise probiotics or prebiotics that inhibit *E. faecalis* and/or promote FUT2 activity (e.g., a recombinant gut microorganism that expresses FUT2).

Disclosed herein are pharmaceutical compositions comprising an oligosaccharide of the disclosure, or a pharmaceutically acceptable salt, polymorph, solvate, or prodrug thereof, as an active ingredient, combined with a pharmaceutically acceptable vehicle, carrier, diluent, or excipient, or a mixture thereof; in combination with one or more pharmaceutically acceptable excipients or carriers.

Disclosed herein are pharmaceutical compositions in modified release dosage forms, which comprises an oligosaccharide of the disclosure, or a pharmaceutically acceptable salt, solvate, or prodrug thereof, and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients or carriers.

Further disclosed herein are pharmaceutical compositions in enteric coated dosage forms, which comprise an oligosaccharide disclosed herein, or a pharmaceutically acceptable salt, polymorph, solvate, or prodrug thereof, and one or more release controlling excipients or carriers for use in an enteric coated dosage form. The pharmaceutical compositions may also comprise non-release controlling excipients or carriers.

An oligosaccharide disclosed herein may be administered alone, or in combination with one or more other active ingredients for treating liver disease. The pharmaceutical compositions that comprise an oligosaccharide disclosed herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy, supra; Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. Moreover, the compositions may be staggered (i.e., before or after) delivery of a second therapeutic compositions (e.g., a probiotic formulation). It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the oligosaccharides may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the oligosaccharides may be given continuously or temporarily suspended for a certain length of time (i.e., a "drug holiday").

Once improvement of the patient's condition has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The pharmaceutical compositions disclosed herein may be formulated in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastimes, cachets, pellets, medicated chewing gum, granules, bulk powders (e.g., dried formulations), effervescent or non-effervescent powders or granules, solutions, emulsions, suspensions, solutions, wafers, sprinkles, elixirs, and syrups. In addition to the oligosaccharides, the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethyl cellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethyl cellulose (HEC), hydroxypropyl cellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions disclosed herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions disclosed herein varies upon the type of formulation, and is readily discernible to those of ordinary skill in the art. The pharmaceutical compositions disclosed herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions disclosed herein may contain about 0.1 to about 5% by weight of a lubricant.

Suitable glidants include colloidal silicon dioxide, CAB—O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate. It should be understood that many carriers and excipients may serve several functions, even within the same formulation.

The pharmaceutical compositions disclosed herein may be formulated as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions disclosed herein may be formulated as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms disclosed herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions disclosed herein may be formulated in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) disclosed herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions disclosed herein for oral administration may be also formulated in the forms of liposomes, micelles, microspheres, or nanosystems. Micellar dosage forms can be prepared as described in U.S. Pat. No. 6,350,458.

The pharmaceutical compositions disclosed herein may be formulated as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions disclosed herein can be formulated as an oral nutritional composition. An oral nutritional composition can contain sources of protein, lipids and/or digestible carbohydrates and can be in solid, powdered or liquid forms. The composition can be designed to be the sole source of nutrition or a nutritional supplement. Suitable protein sources include intact, hydrolyzed, and partially hydrolyzed protein, which can be derived from any suitable source such as milk (e.g., casein, whey), animal (e.g., meat, fish), cereal (e.g., rice, corn), and vegetable (e.g., soy, potato, pea), insect (e.g., locust) and combinations of these sources. Examples of the source of protein include whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, non-fat dry milk, condensed skim milk, soy protein concentrates, soy protein isolates, soy protein hydrolysates, pea protein concentrates, pea protein isolates, pea protein hydrolysates, collagen proteins, and combinations of these sources.

The pharmaceutical compositions disclosed herein may be formulated as immediate or modified release dosage forms, including delayed-, sustained, pulsed-, controlled, targeted-, and programmed-release forms.

The pharmaceutical compositions disclosed herein may be co-formulated with other active ingredients which do not impair the desired therapeutic action, or with substances that supplement the desired action.

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic and/or fungistatic concentrations. All parenteral formulations must be sterile, as known and practiced in the art.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

The pharmaceutical compositions disclosed herein may be administered topically to the skin, orifices, or mucosa. The topical administration, as used herein, include (intra)

dermal, conjunctival, intracorneal, intraocular, ophthalmic, auricular, transdermal, nasal, vaginal, ureteral, respiratory, and rectal administration.

The pharmaceutical compositions disclosed herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions disclosed herein may also comprise liposomes, micelles, microspheres, nanosystems, and mixtures thereof.

Pharmaceutically acceptable carriers and excipients suitable for use in the topical formulations disclosed herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions disclosed herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and derivatives thereof.

The pharmaceutical compositions disclosed herein in a modified release dosage form may be prepared by methods known to those skilled in the art, including direct compression, dry or wet granulation followed by compression, melt-granulation followed by compression.

Provided herein are oligosaccharides that provide biological and therapeutic effect in treating liver disease, in particular, alcohol-induced liver disease. The studies presented herein indicate that oral administration of an oligosaccharide of the disclosure (e.g., 2'-FL) can be used to treat liver disease in in vivo models. While the foregoing clearly establishes the efficacy of using an oligosaccharide of the disclosure to treat alcohol-induced liver disease, it should be understood that protective effects of the oligosaccharides of the disclosure are generally efficacious for use with other liver disorders by maintaining a healthy intestinal state. In view thereof, the disclosure provides for methods of treating a subject with liver disease comprising administering to the subject an effective amount of an oligosaccharide of the disclosure, or a pharmaceutically acceptable salt, solvate, or prodrug thereof. In an alternate embodiment, the disclosure provides methods for treating, preventing, or ameliorating one or more symptoms of a liver disease comprising administering to a subject having or being suspected of having such a liver disease, a therapeutically effective amount of an oligosaccharide as disclosed herein, or a pharmaceutically acceptable salt, solvate, or prodrug thereof. In still another embodiment, the disclosure provides a method of treating a subject having, suspected of having or at risk of having a liver disease (e.g., alcoholic liver disease) comprising administering an oligosaccharide of the disclosure (e.g., a 2'FL or composition containing 2'FL) and one or more agents that (i) inhibit *E. faecalis* growth, (ii) inhibit cytolysin activity, and/or (iii) a probiotic that inhibits *E. faecalis*. In a further embodiment, the disclosure provides a method of monitoring the progression of a treatment with according to any of the foregoing comprising (i) measuring *E. faecalis* in the intestine or stool, (ii) measuring cytolysin activity and/or (iii) measuring FUT2 activity in a subject undergoing therapy. In one embodiment, the measuring can be performed prior to administration of a composition comprising 2'FL and then measured after administration of a composition comprising 2'FL to determine whether the 2'FL is promoting intestinal balance by inhibiting *E. faecalis* and/or cytolysin. The method can also be used to predict whether a subject undergoing 2'FL therapy will have improved liver function.

In one embodiment, the liver disease that can be treated by an oligosaccharide of the disclosure is caused by excessive alcohol consumption, or ingestion of harmful chemicals (e.g., vinyl chloride), heavy metals, polychlorinated biphenyls (PCBs), pesticides, etc. It is postulated herein that patients with liver disease caused by excessive alcohol consumption (or ingestion of harmful chemicals), leads to a loss of $\alpha$1-2-fucosylated glycans (sugar molecules) on the surface of intestinal epithelial cells (glycocalyx). Intestinal bacteria usually thrive on these glycans by using them as energy substrates. In the absence of these specific glycans, some bacteria lose their competitive advantage and other bacteria grow and thrive instead, changing the gut microbiome, which contributes to symptoms of the liver disease. In particular, oral administration of an oligosaccharide of the disclosure can compensate for the loss of $\alpha$1-2-fucosylated glycans on the surface of intestinal epithelial cells brought about by exposure to alcohol or harmful chemicals, thereby preventing or treating the liver disease caused thereby. Thus, the oligosaccharide of the disclosure may work as a prebiotic, compensating for the loss of intestinal $\alpha$1-2-fucosylated glycans and serving as metabolic substrate for specific microbes that are beneficial for liver health, while suppressing or inhibiting the growth bacteria that are harmful to liver health. However, the oligosaccharides of the disclosure can also be absorbed directly and be found in systemic circulation thereby treating liver disease pathogenesis independent of the gut microbiome. It will also be recognized that use of the oligosaccharide can be complemented or used in conjunction with probiotics that promote normal intestinal microbiome balance and/or inhibitors of *E. faecalis*.

Generally, the amount of an oligosaccharide disclosed herein required to be administered to the person can vary depending upon factors such as the risk and condition severity, the age of the person, the form of the composition, and other medications being administered to the person. It would be expected that an oligosaccharide described herein should be well tolerated irrespective of the age and condition of the subject. The dosage of oligosaccharide to be administered can readily be set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day or any mg value between any of the foregoing ranges. An appropriate dose can be determined based on several factors, including, for example, the body weight and/or condition of the patient being treated, the severity of the condition, being treated, other ailments and/or diseases of the person, the incidence and/or severity of side effects and the manner of administration. Appropriate dose ranges can be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

Depending on the liver disease to be treated and the subject's condition, an oligosaccharide as disclosed herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration. Typically, the oligosaccharide will be administered orally.

The dose may be in the form of one, two, three, four, five, six, or more sub-doses that are administered at appropriate intervals per day. The dose or sub-doses can be administered in the form of dosage units containing from about 0.01 to about 2 grams, from about 0.05 to about 1 gram, or from about 10 to about 500 milligrams active ingredient(s) per dosage unit.

In certain embodiments, an appropriate dosage level is about 0.005 to about 1 g/kg patient body weight per day, about 0.01 to about 5 g/kg patient body weight per day, about 0.01 to about 1 g/kg per day, about 0.01 to about 0.5 g/kg per day, or about 0.1 to about 500 mg/kg per day, which may be administered in single or multiple doses. A suitable dosage level may be about 0.1 to about 500 mg/kg per day, about 0.1 to about 250 mg/kg per day, or about 0.1 to about 100 mg/kg per day. Within this range the dosage may be about 0.01 to about 0.1, about 0.1 to about 1.0, about 1.0 to about 10, or about 10 to about 100 mg/kg per day.

The oligosaccharides disclosed herein may also be combined or used in combination with other agents useful in the treatment, prevention, or amelioration of one or more symptoms of an autoimmune disorder and/or inflammatory disorder. By way of example only, the therapeutic effectiveness of one of the oligosaccharides described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefore, simultaneously or sequentially with an oligosaccharide as disclosed herein. When an oligosaccharide as disclosed herein is used contemporaneously with one or more other drugs, a pharmaceutical composition containing such other drugs in addition to an oligosaccharide disclosed herein may be utilized, but is not required. Accordingly, the pharmaceutical compositions disclosed herein include those that also contain one or more other active ingredients or therapeutic agents, in addition to an oligosaccharide disclosed herein.

In certain embodiments, an oligosaccharide disclosed herein can be combined with one or more liver disease treatments known in the art, including, but not limited to, corticosteroids, pentoxifylline, cysteamine and/or cystamine (including enteric formulations thereof), probiotics and the like.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more oligosaccharides described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise an oligosaccharide with an identifying description or label or instructions relating to its use in the methods described herein. In certain embodiments, a container consists of 2'FL and optionally 3'SL and/or 6'SL or a combination of 2'FL, 3'SL and 6'SL. In other embodiments, the container comprise or consists of 2'FL and optionally 3'SL and/or 6'SL or a combination thereof at 145 mg/L or greater. In another embodiment, the container comprises a composition that is at least 9% (e.g., 10, 15, 20, 25, 30, 35, 40, 45, 50, 55, 60, 65, 70, 75, 80, 85, 90, 95, or 100%; or any value between any of the foregoing) 2'FL of the total oligosaccharides in the composition.

A kit will typically comprise one or more additional containers, each with one or more of various materials (such as reagents, optionally in concentrated form, additional active ingredients such as a probiotic and/or cysteamine/cystamine, and/or devices) desirable from a commercial and user standpoint for use of an oligosaccharide or therapy described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Animal models. Fut2 deficient (Fut2$^{-/-}$) mice on a C57BL/6 background were used in the experiments. Heterozygous mice were used for breeding. Immunohistochemistry with biotinylated *Ulex Europaeus* Agglutinin I (see below) confirmed the absence of α1-2-fucosylated glycans in the intestine of Fut2$^{-/-}$ mice (not shown). Age-matched Fut2 knockout and wild type (WT) littermate mice (8-week, female mice) were given Lieber DeCarli diet (LD101A, TestDiet) for 9 weeks. In brief, the caloric intake from ethanol was increased gradually, 0% on day 1, 10% on day 2 and 3, 20% on day 4 and 5, 30% from day 6 to the end of week 6, 36% from week 7 to week 9. Pair-fed control mice received a diet with an isocaloric substitution of isomaltose.

In the 2'-fucosyllactose (2'-FL; a gift from Jennewein Biotechnologie GmbH, Germany) supplementation experiments we used a chronic-binge ethanol diet (NIAAA model). Fut2$^{-/-}$ mice (10-11 weeks, male and female) were fed with Lieber-DeCarli diet with caloric intake from ethanol 0% on days 1-5 and 36% of total calories from day 6 to day 16. At day 16 in the early morning, mice were gavaged with a single dose of ethanol (5 g/kg body weight) and harvested 9 hours later. In the 2'-FL treated groups 2'-FL was added in the ethanol diet at a final concentration of 2 mg/mL and given continuously during the study period.

Patient cohorts. Patients with alcohol use disorder (AUD) were diagnosed according to the DSM IV criteria and a detailed description has been published. Patients with alcohol use disorder (n=10) or non-alcoholic controls (n=11) underwent an upper gastrointestinal endoscopy (EGD) with duodenal biopsies if clinically indicated as part of routine clinical care. To preserve the mucus layer, duodenal biopsies obtained during an upper endoscopy were fixed in Carnoy's fixative consisting of 60% Ethanol, 30% Chloroform, and 10% Glacial acetic acid for 1h. Written informed consent was obtained from all patients and controls. The study protocol was approved by each center involved in enrolling patients.

Staining procedures. Paraffin-embedded sections were deparaffinized by xylene and rehydration in concentration gradients of ethanol. The sections were immersed in 0.1% $H_2O_2$(Sigma-Aldrich, H1009) for 30 min and then blocked with avidin and biotin (Vector, SP-2002) for 15 min each. After blocking with 1% bovine serum albumin for 5 min, sections were incubated with biotinylated *Ulex Europaeus* Agglutinin I (UEA, Vector, B-1065) overnight at 4° C. Sections were then washed with TBST, and incubated with Streptavidin, Horseradish Peroxidase for 30 min. Then the sections were stained by DAB solution (Vector, SA-5004) for 2 min, and hematoxylin for 1 min for counterstaining. A negative staining control was performed by using PBS instead of UEA.

Formalin-fixed and paraffin-embedded mouse livers were stained with hematoxylin-eosin (Leica Biosystems Inc.) using standard staining protocols. Frozen liver sections were stained with Oil Red O (Sigma-Aldrich, 00625).

Biochemical assays. Levels of plasma alanine aminotransferase (ALT) were measured using infinity ALT kit (Thermo Scientific, TR71121). Triglyceride levels were measured using the Triglyceride Liquid Reagents Kit (Pointe Scientific, 51604).

Reverse transcription and real-time quantitative PCR. For reverse transcription qPCR, RNA was extracted from mouse liver, and cDNAs were generated as described. DNA from mouse feces was extracted using QIAamp Fast DNA Stool kit (Qiagen, 51604). Quantitative PCR was performed with iTaq universal SYBR Green Supermix (Bio-Rad, 1725124) using a StepOnePlus thermocycler real-time PCR system. Primer sequences for mouse genes were obtained from the NIH qPrimerDepot. The values of mouse genes were normalized to 18S, while bacterial genes were normalized to 16S.

Immunoblotting. Liver tissue was homogenized in RIPA buffer, supplemented with protease inhibitor, and used for immunoblotting. Immunoblot analysis was performed as described using Anti-Cytochrome P450 Enzyme (Cyp2e1) (Millipore, ab1252) and β-actin (Sigma-Aldrich, A2228) antibodies.

*Enterococcus faecalis* cultures. A cytolysin positive strain of *E. faecalis*, which was isolated from feces of an ethanol-fed Atp4a$^{s1/s1}$ mouse, was cultured in BHI media with 0, 0.25, 0.5, 1, 2 or 20 mg/mL of 2'-FL in triplicate for each concentration. Sampling was taken at 30 min intervals during the course of 6 h. Cell growth was determined by measuring the optical density at 600 nm for each time-point.

Statistical analysis. All data were expressed as mean±SEM. For comparison of two groups, the Student's unpaired t-test was used. For comparisons of >2 groups between ethanol diet groups, two-way analysis of variance (ANOVA) was used followed by Tukey's post-hoc test. Analysis was performed with GraphPad Prism V.7.0. A P value <0.05 was considered significant.

Patients with alcohol use disorder have decreased intestinal α1-2-fucosylation. To evaluate the role of intestinal α1-2-fucosylation, UEA staining of duodenal biopsies from non-alcoholic controls and patients with alcohol use disorder was performed. Patients with alcohol use disorder had an obvious lower expression of α1-2-fucosylation on duodenal biopsies as compared with non-alcoholic controls (e.g., see FIG. 1). This indicates that chronic alcohol consumption down-regulates intestinal α1-2-fucosylation in humans.

Figure 2A:
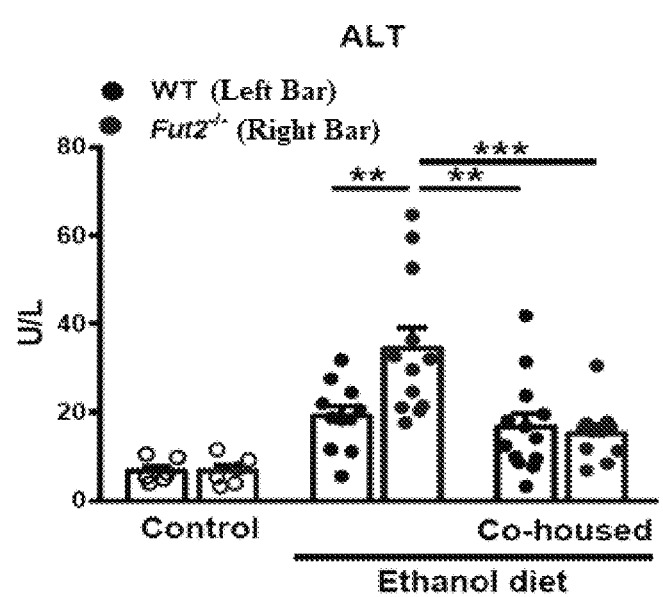
FIG. 2A-G shows that Fut2 deficiency exacerbates chronic ethanol-induced liver disease in mice. $Fut2^{-/-}$ and wild type (WT) littermates were fed with either control diet or ethanol-containing Lieber DeCarli diet for 9 weeks. (A) Plasma alanine aminotransferase (ALT). (B) Representative images of H&E-stained liver tissue. (C) Hepatic triglycerides levels. (D) Representative images of Oil Red O-stained liver tissue. (E) Hepatic Il1b mRNA. (F) Hepatic Cxcl1 mRNA. (G) Hepatic Cxcl2 mRNA. Data represent mean±SEM; *,  and * indicate P<0.05, P<0.01 and P<0.001, respectively. Scale bar=50 μm. Experiments performed in n=5-8 in control diet groups and n=11-13 in ethanol diet groups. For the H&E and Oil Red O staining, n=5 per group.
Figure 2B:
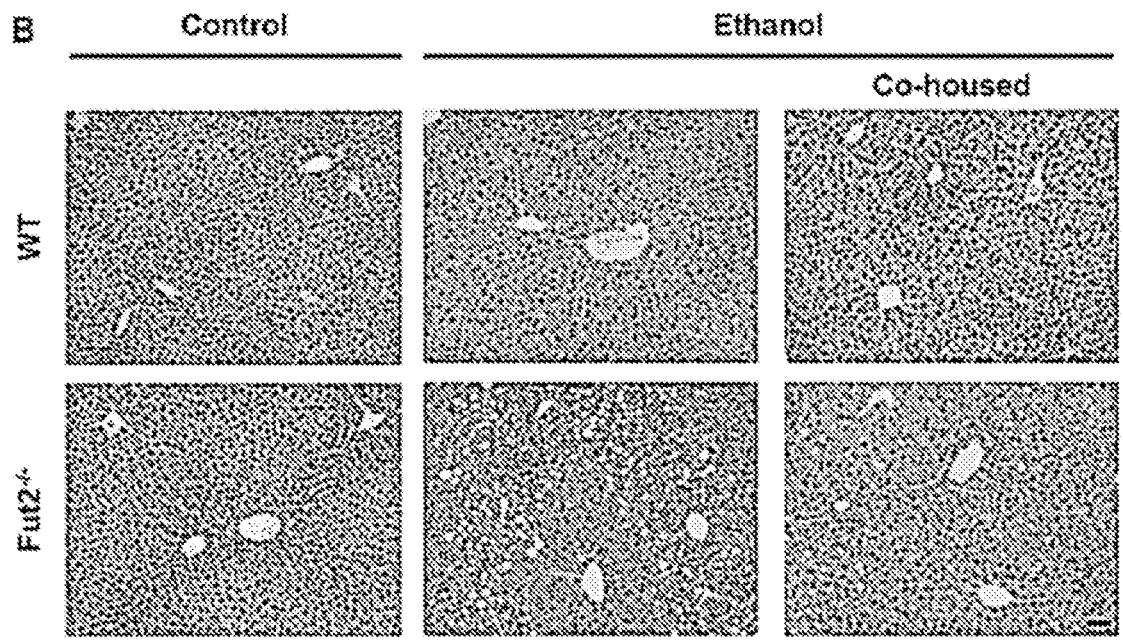
Figure 2C:
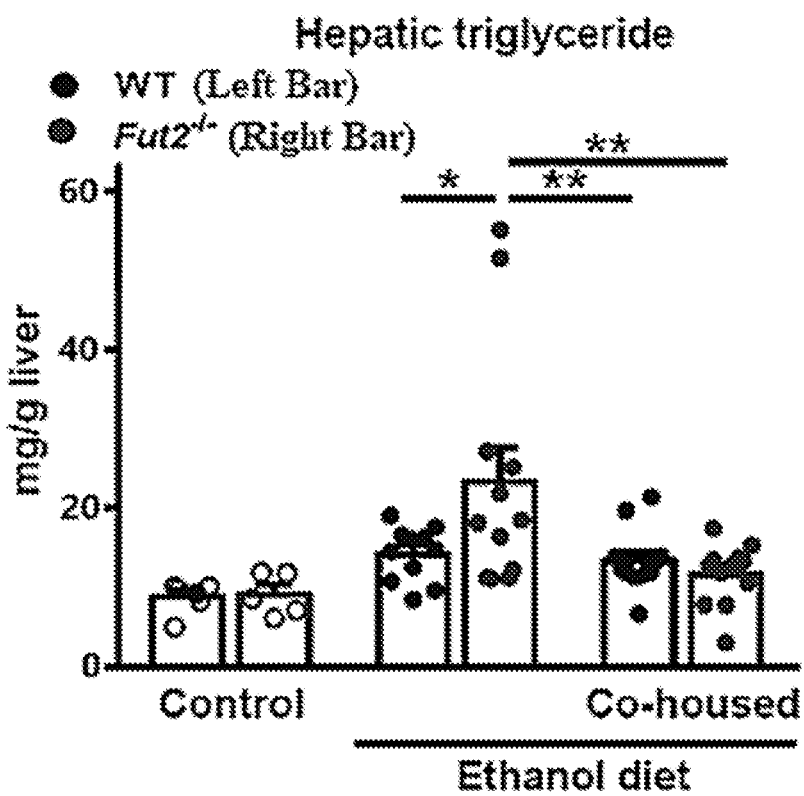
Figure 2D:
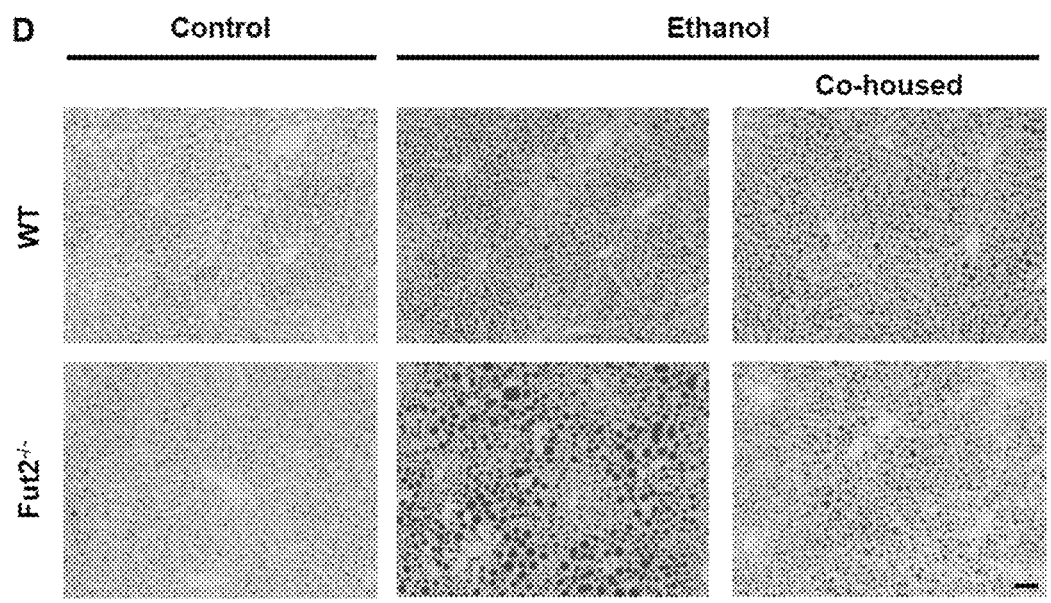
Figure 2E:
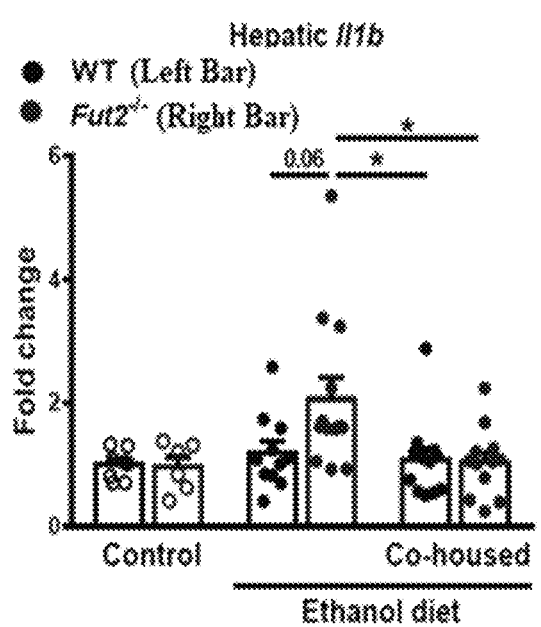
Figure 2F:
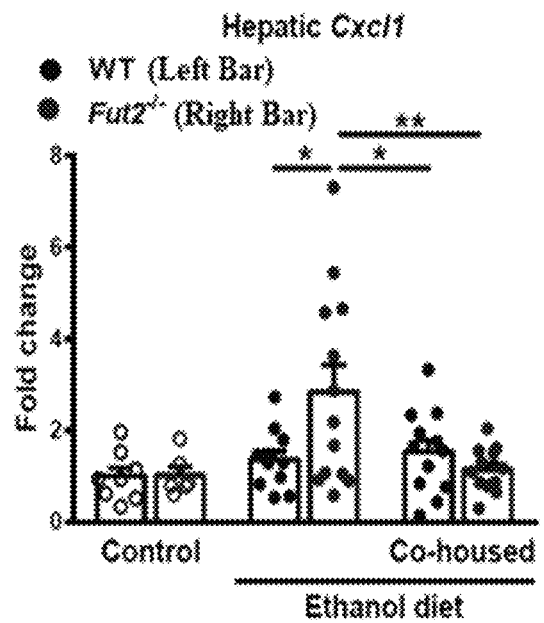
Figure 2G:
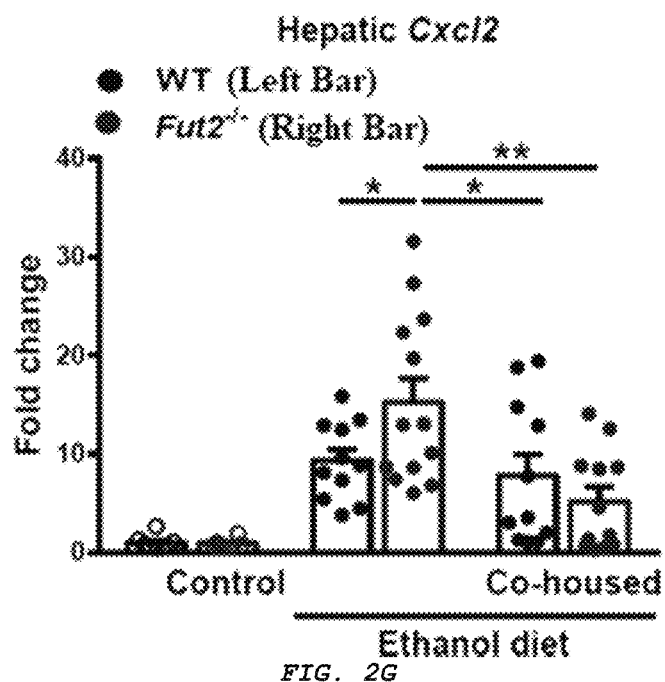

Fut2 deficiency exacerbates chronic ethanol-induced liver disease in mice. To further investigate α1-2-fucosylation for pathogenesis of chronic ethanol-induced liver disease, Fut2 deficient and WT littermate mice were subjected to feeding of an ethanol diet for 9 weeks. Fut2$^{-/-}$ mice had more severe ethanol-induced liver injury, indicated by elevated level of plasma ALT (e.g., see FIG. 2A) and liver histopathology (e.g., see FIG. 2B), and increased hepatic steatosis as evidenced by higher hepatic triglyceride (e.g., see FIG. 2C) and oil red o staining (e.g., see FIG. 2D) when compared with WT mice. Fut2$^{-/-}$ mice also had more liver inflammation as evidenced by higher expression of hepatic inflammatory genes, like Interleukin-1 beta (Il1b), chemokine (C—X—C motif) ligand 1 (Cxcl1) and Cxcl2 (e.g., FIG. 2E-2G).

Figure 3A:
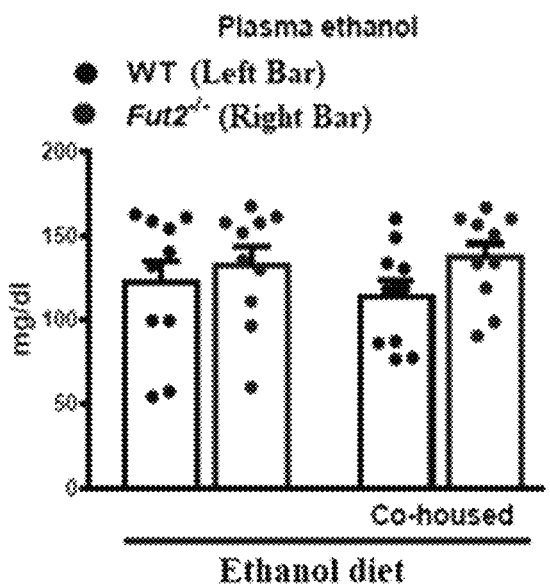
FIG. 3A-C examines the metabolism of ethanol. $Fut2^{-/-}$ and wild type (WT) littermates were fed with either control diet or ethanol-containing Lieber DeCarli diet for 9 weeks. (A) Plasma ethanol. (B) Hepatic Adh1 mRNA. (C) Immunoblot analysis of hepatic Cyp2e1. Experiments performed in n=6-8 in control diet groups and n=10-13 in ethanol diet groups.
Figure 3B:
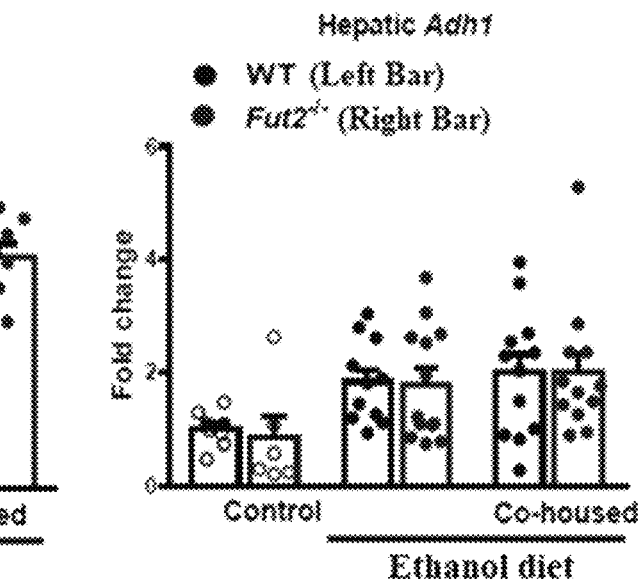
Figure 3C:
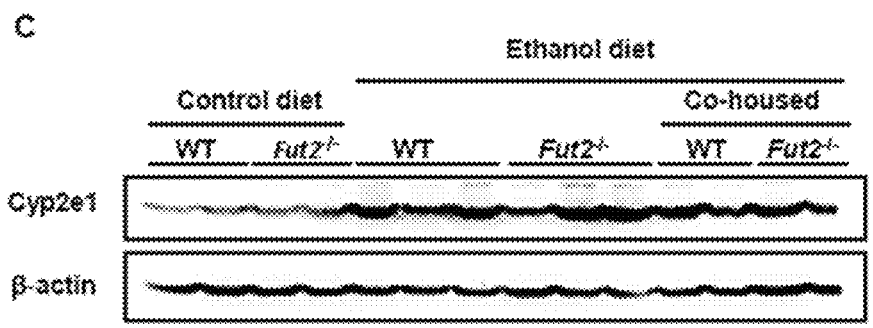

To determine whether Fut2 deficiency alters absorption and hepatic metabolism of ethanol, several ethanol metabolism related parameters were measured. Plasma ethanol levels were not different between WT and Fut2$^{-/-}$ ethanol diet-fed mice (e.g., see FIG. 3A). Two major enzymes that metabolize ethanol in the liver are alcohol dehydrogenase-1 (Adh1) and Cyp2e1. Hepatic Adh1 mRNA and Cyp2e1 protein were similar between WT and Fut2$^{-/-}$ ethanol diet-fed mice (e.g., see FIGS. 3B and 3C).

Taken together, these data demonstrate that Fut2 deficiency exacerbates chronic ethanol-induced liver disease in mice and this effect was not through an altered ethanol metabolism.

Co-housing ameliorates the disease promoting effect in ethanol-fed Fut2 deficient mice. Since intestinal α1-2-fucosylation is important for host-microbiota interaction, WT and Fut2$^{-/-}$ mice were co-housed during ethanol administration. Co-housing results in fecal microbiota transfer between mice in the same cage. Co-housing of WT littermates and Fut2$^{-/-}$ mice conferred protection from features of ethanol diet-induced liver disease to Fut2$^{-/-}$ mice (e.g., see FIGS. 2 and 3), indicating that the phenotype is transmissible via microbiota transfer.

Figure 4A:
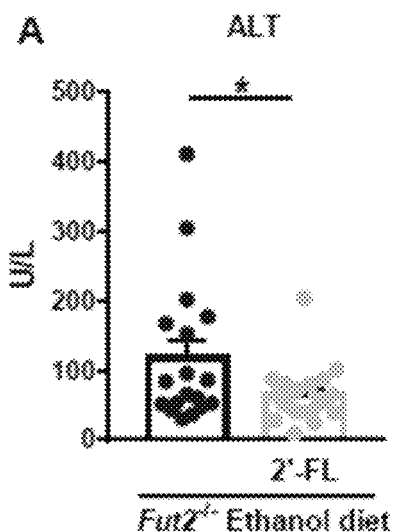
Figure 4B:
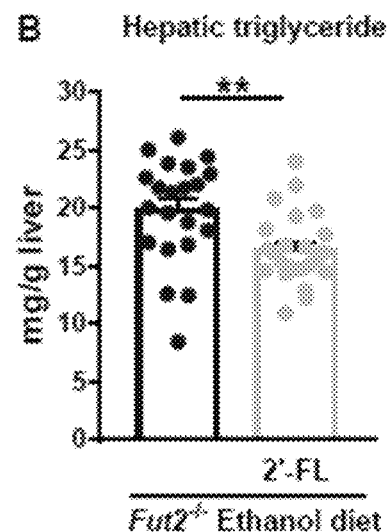
Figure 4C:
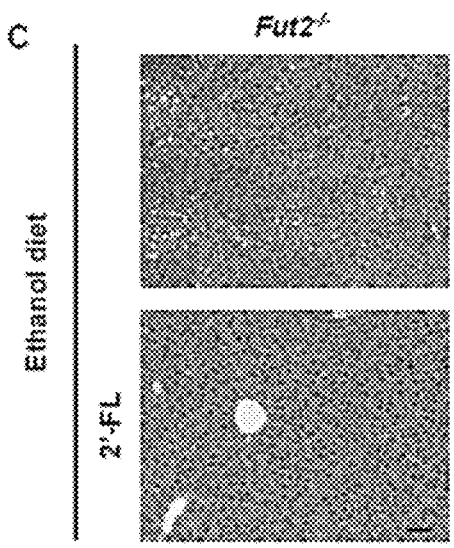
Figure 4D:
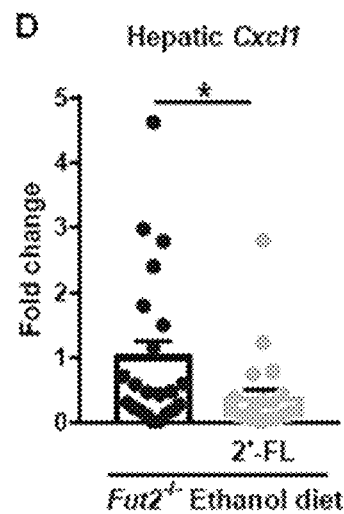
Figure 4E:
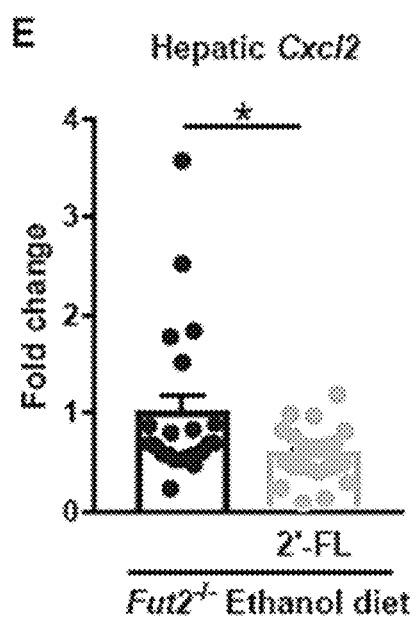
Figure 4F:
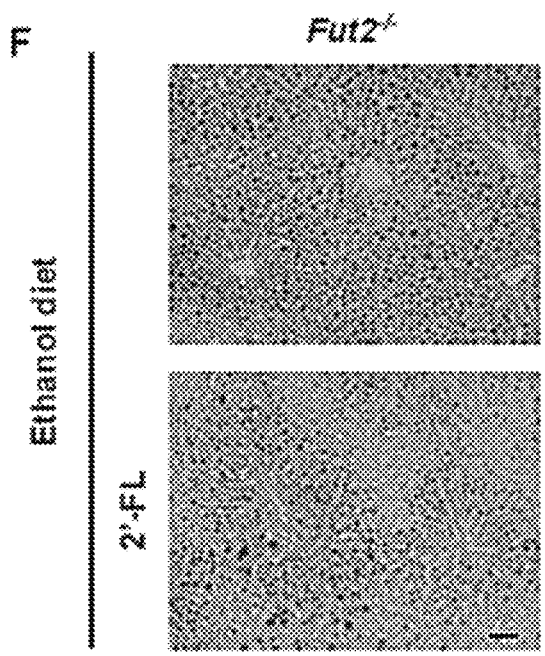
Figure 4G:
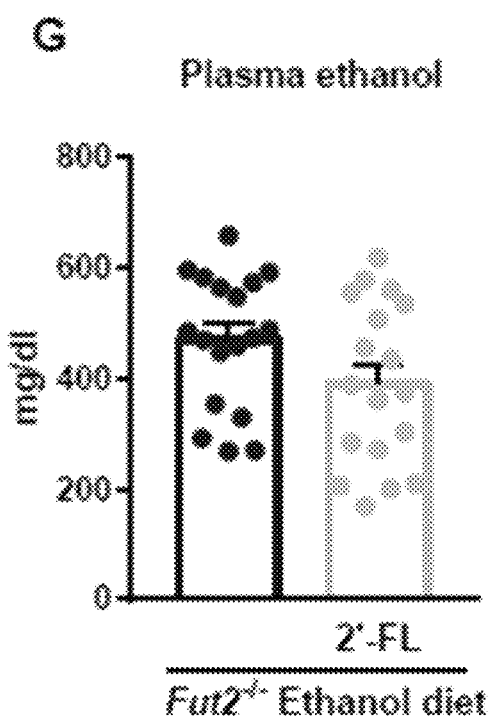
Figure 4H:
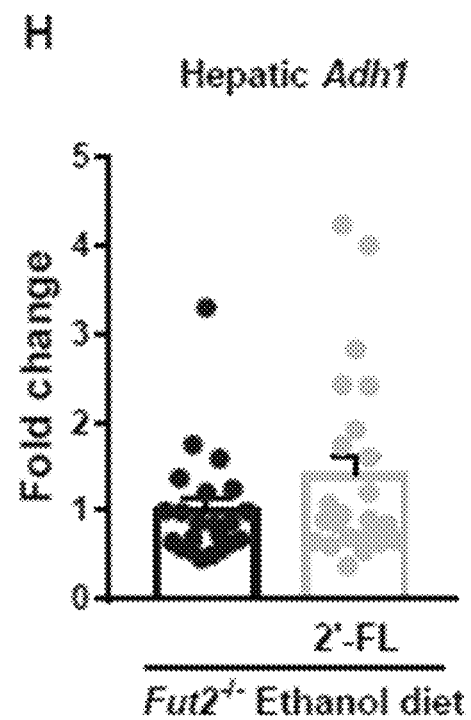

Supplementation of the exogenous α1-2-fucosylated glycan 2'fucosyllactose (2'FL) attenuates ethanol-induced liver disease in mice. To test whether intestinal α1-2-fucosylation could be restored in Fut2 deficient mice, 2'-fucosyllactose (2'-FL) was supplemented in the liquid diet of Fut2$^{-/-}$ mice during chronic ethanol feeding. 2'-FL is an α1-2-fucosylated oligosaccharide that is highly abundant in breast milk of secretor women and serves as a prebiotic that can be cleaved and used as substrate and energy source by intestinal bacteria. Dietary supplementation of 2'-FL in Fut2$^{-/-}$ mice decreased ALT, hepatic steatosis and inflammation as evidenced by lower ALT (e.g., see FIG. 4A), hepatic triglyceride (e.g., see FIG. 4B), improvement in liver histopathology (e.g., see FIG. 4C) and Oil Red O staining (e.g., see FIG. 4F), and decreased mRNA level of hepatic inflammatory genes including Cxcl1 and Cxcl2 (e.g., see FIGS. 4D and 4E) compared with Fut2$^{-/-}$ mice fed an ethanol diet alone. Restoration of intestinal α1-2-fucosylation ameliorates ethanol-induced liver disease in Fut2$^{-/-}$ mice without affecting metabolism of ethanol (e.g., see FIG. 4G-4I). These findings indicate that Fut2-mediated intestinal α1-2-fucosylation is critical in ethanol-induced liver disease.

Figure 5C:
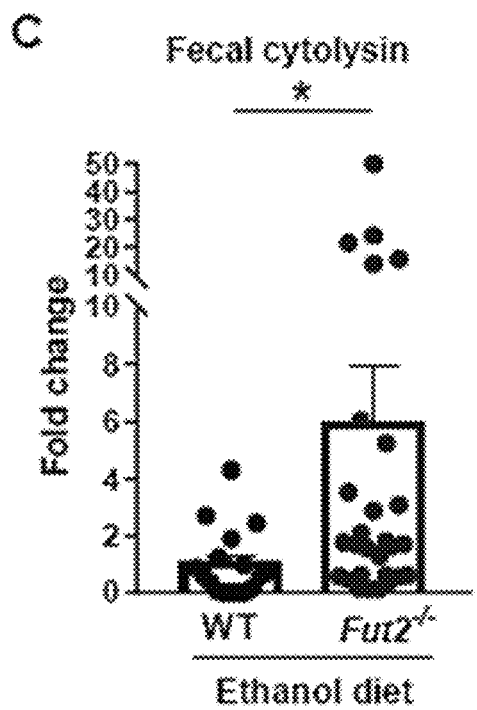
Figure 5D:
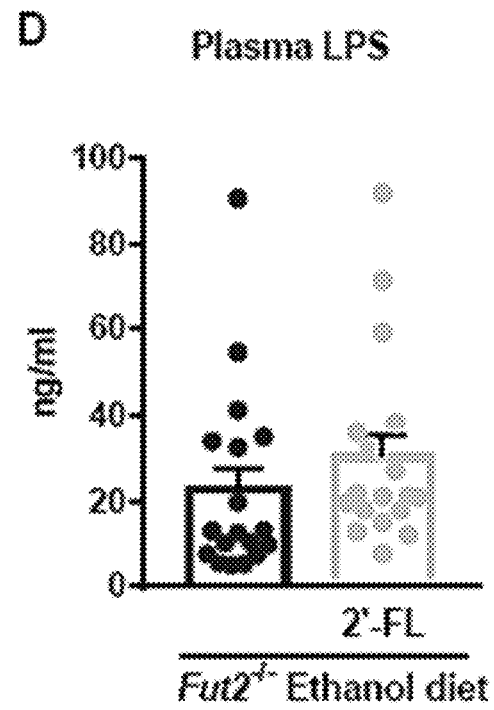

Intestinal α1-2-fucosylation prevents intestinal colonization of cytolysin positive *Enterococcus faecalis* in ethanol diet-fed mice. Translocated endotoxin derived from intestinal bacteria contributes of ethanol-induced liver disease in mice. WT and Fut2$^{-/-}$ mice showed similar levels of plasma lipopolysaccharides (LPS) after chronic ethanol feeding (e.g., see FIG. 5A). Consistently, 2'-FL supplementation did not affect plasma LPS levels (e.g., see FIG. 5D). This indicates that the protective effect of α1-2-fucosylation was not through decreasing paracellular permeability in the intestine.

Figure 5E:
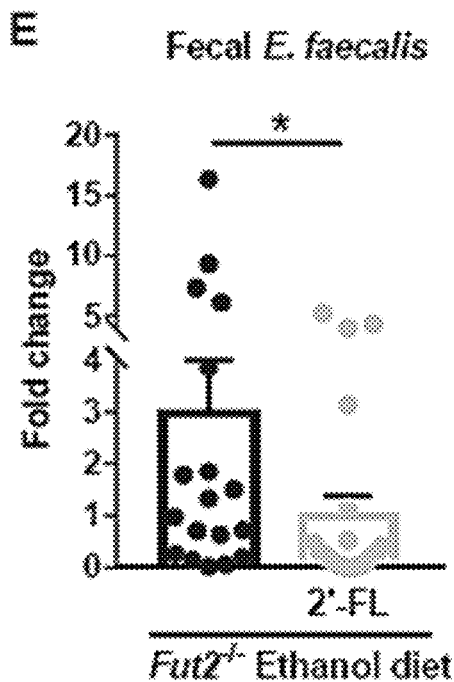

Experimental expansion of intestinal *E. faecalis* by gavage during ethanol feeding exacerbates ethanol-induced liver disease in mice. To evaluate the role of *E. faecalis* in ethanol-induced liver disease in Fut2 deficient mice, fecal *E. faecalis* was quantified by qPCR. After ethanol feeding, Fut2$^{-/-}$ mice had significantly higher levels of fecal *E. faecalis* compared with WT mice (e.g., see FIG. 5B). Dietary supplementation of the prebiotic 2'-FL decreased the intestinal amount of *E. faecalis* in Fut2$^{-/-}$ mice (e.g., see FIG. 5E). This result was consistent with a previous study, which reported that intestinal α1-2-fucosylation enhances resistance to colonization of *E. faecalis* in the colonic lumen and mucosa.

Figure 5F:
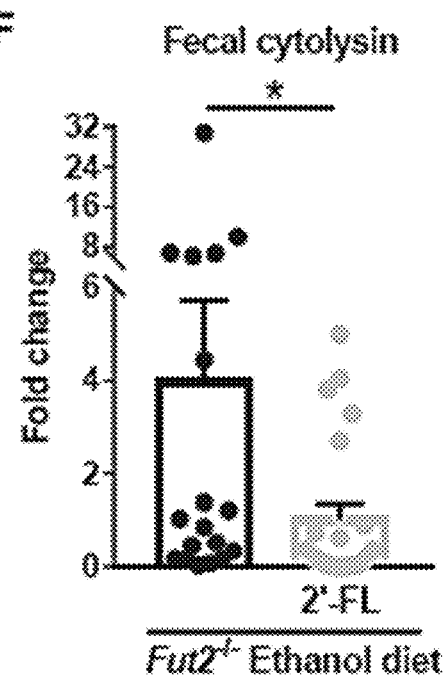

The association of cytolysin expression with increased toxicity of *E. faecalis* infections had been established in many animal and clinical studies. Importantly, mice gavaged with *E. faecalis* expressing the exotoxin cytolysin had more severe ethanol-induced liver disease than those gavaged with cytolysin-negative *E. faecalis*. Based on these findings fecal cytolysin was quantified. It was found that Fut2$^{-/-}$ mice fed ethanol diet had higher levels of fecal cytolysin than ethanol diet-fed WT mice (e.g., see FIG. 5C). 2'-FL supplementation decreased fecal cytolysin in Fut2$^{-/-}$ mice following chronic-binge ethanol feeding (e.g., see FIG. 5F). Taken together, increased intestinal cytolytic *E. faecalis* might contribute to more severe ethanol-induced liver disease observed in Fut2$^{-/-}$ mice.

Figure 5G:
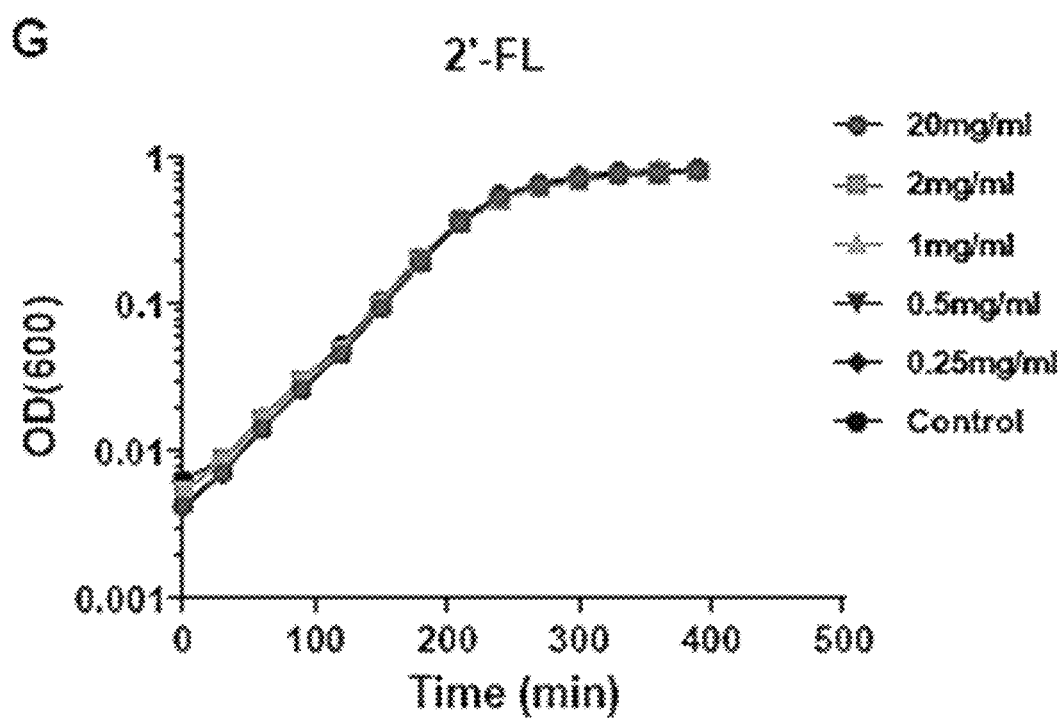

Growth of *E. faecalis* is not affected by 2'-FL. In order to investigate the direct effect of 2'-FL on the growth of cytolytic *E. faecalis*, a strain of cytolytic *E. faecalis* was incubated with different concentrations of 2'-FL in the culture medium. The results showed that *E. faecalis* growth was not affected by supplementation with different concentrations of 2'-FL, which indicates that 2'-FL does not directly inhibit the growth of cytolytic *E. faecalis* (e.g., see FIG. 5G).

It will be understood that various modifications may be made without departing from the spirit and scope of this disclosure. Accordingly, other embodiments are within the scope of the following claims.

What is claimed is:

1. A method for treating a subject with alcohol induced liver disease, comprising administering to the subject an effective amount of a composition comprising an oligosaccharide with a structure of Formula I:

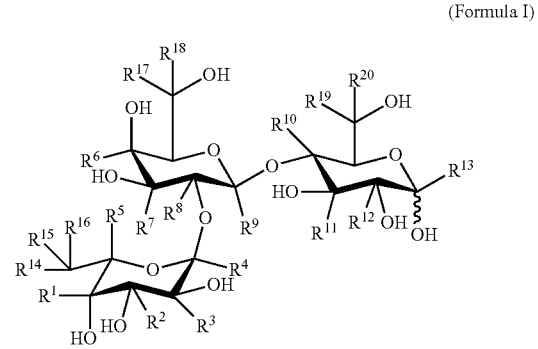

(Formula I)

or a pharmaceutically acceptable salt, polymorph, solvate, or prodrug thereof, wherein:

R$^1$-R$^{20}$ are independently selected from the group consisting of H, D, halo, azide, nitro, amine, aldehyde, alkoxy, ketone, ester, carboxylic acid, hydroxyl, substituted or non-substituted (C$_1$-C$_6$)alkyl, substituted or non-substituted (C$_1$-C$_6$)heteroalkyl, substituted or non-substituted (C$_2$-C$_6$)alkenyl, substituted or non-substituted (C$_2$-C$_6$)heteroalkenyl, optionally substituted or non-substituted (C$_2$-C$_6$)alkynyl, substituted or non-substituted (C$_2$-C$_6$)heteroalkynyl, and heterocycle; and wherein the effective amount is obtained to inhibit fecal *Enterococcus faecalis* and/or cytolysin in the presence of alcohol.

2. The method of claim 1, wherein the oligosaccharide comprises a structure of Formula 1(a):

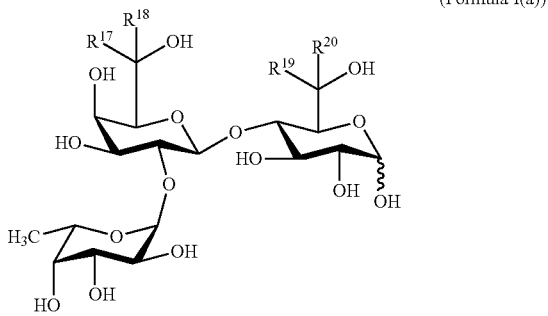

(Formula I(a))

or a pharmaceutically acceptable salt, polymorph, solvate, or prodrug thereof, wherein:

$R^{17}$-$R^{20}$ are independently selected from the group consisting of H, D, halo, azide, nitro, amine, aldehyde, alkoxy, ketone, ester, carboxylic acid, hydroxyl, substituted or non-substituted ($C_1$-$C_6$)alkyl, substituted or non-substituted ($C_1$-$C_6$)heteroalkyl, substituted or non-substituted ($C_2$-$C_6$)alkenyl, substituted or non-substituted ($C_2$-$C_6$)heteroalkenyl, substituted or non-substituted ($C_2$-$C_6$)alkynyl, substituted or non-substituted ($C_2$-$C_6$)heteroalkynyl, and heterocycle.

3. The method of claim 2, wherein the oligosaccharide comprises a structure of Formula 1(b):

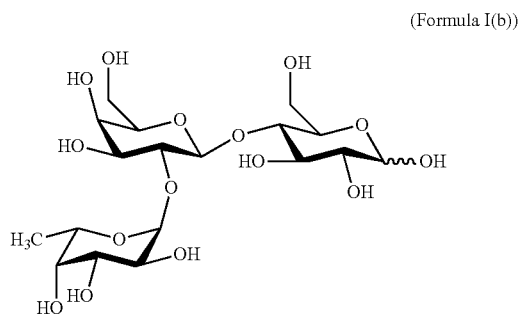

(Formula I(b))

or a pharmaceutically acceptable salt, polymorph, solvate, or prodrug thereof.

4. The method of claim 1, wherein the composition is orally administered to the subject.

5. The method of claim 4, wherein the composition is a nutritional composition.

6. The method of claim 4, wherein the composition is formulated as a tablet or a capsule.

7. The method of claim 5, wherein the composition comprises at least 9% by weight of the oligosaccharide in the nutritional composition.

8. The method of claim 1, wherein the alcohol-induced liver disease is caused by chronic and/or excessive alcohol consumption.

9. The method of claim 1, wherein the composition is administered sequentially or concurrently with one or more other liver disease treatments.

10. The method of claim 9, wherein one or more other liver disease treatments are selected from corticosteroids, pentoxifylline, cysteamine and/or cystamine.

11. A method to restore or compensate for the loss α1-2-fucosylated glycans on the surface of a subject's intestinal epithelial cells caused by excessive and/or chronic alcohol consumption, comprising:

administering to the subject an effective amount of an oligosaccharide of Formula I, or a composition comprising an effective amount of an oligosaccharide of Formula I:

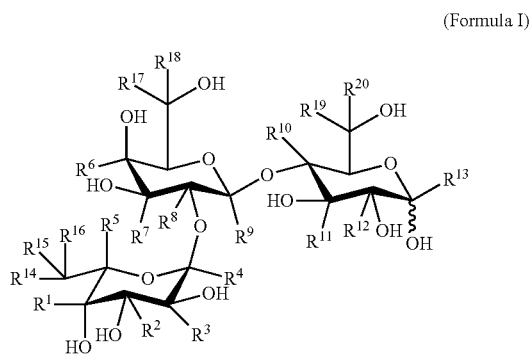

(Formula I)

or a pharmaceutically acceptable salt, polymorph, solvate, or prodrug thereof, wherein:

$R^1$-$R^{20}$ are independently selected from the group consisting of H, D, halo, azide, nitro, amine, aldehyde, alkoxy, ketone, ester, carboxylic acid, hydroxyl, substituted or non-substituted ($C_1$-$C_6$)alkyl, substituted or non-substituted ($C_1$-$C_6$)heteroalkyl, substituted or non-substituted ($C_2$-$C_6$)alkenyl, substituted or non-substituted ($C_2$-$C_6$)heteroalkenyl, substituted or non-substituted ($C_2$-$C_6$)alkynyl, substituted or non-substituted ($C_2$-$C_6$)heteroalkynyl, and heterocycle; and wherein the effective amount is obtained to inhibit fecal *Enterococcus faecalis* and/or cytolysin in the presence of alcohol.

12. The method of claim 11, wherein the oligosaccharide comprises a structure of Formula 1(b):

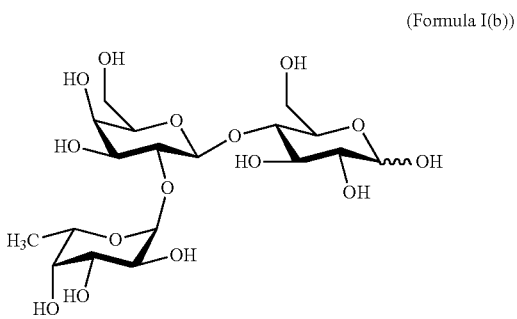

(Formula I(b))

or a pharmaceutically acceptable salt, polymorph, solvate, or prodrug thereof.

13. The method of claim 11, wherein the oligosaccharide or the composition is orally administered to the subject.

14. The method of claim 13, wherein the oligosaccharide is part of a nutritional composition.

15. The method of claim 13, wherein the composition is formulated as a tablet or a capsule.

16. The method of claim 14, wherein the composition comprises at least 9% by weight of the oligosaccharide in the composition.

17. The method of claim 11, further comprising administering a probiotic intestinal composition.

18. The method of claim 11, further comprising administering an agent that inhibits *Enterococcus faecalis* growth.

19. The method of claim 11, further comprising administering an agent for inhibiting the biological activity of cytolysin in the gut of the subject.

* * * * *